United States Patent [19]

Sanderson

[11] Patent Number: 4,583,643
[45] Date of Patent: Apr. 22, 1986

[54] STERILE BAG

[76] Inventor: Roger S. Sanderson, 24662 Santa Clara, Dana Point, Calif. 92629

[21] Appl. No.: 483,266

[22] Filed: Apr. 8, 1983

[51] Int. Cl.[4] .................. B65D 33/01; B65D 81/18
[52] U.S. Cl. .................. 206/438; 206/370; 206/439; 206/484.1; 220/209; 383/44
[58] Field of Search ............ 206/210, 213.1, 363–370, 206/438–440, 484.1, 484.2, 524.8; 220/87, 201, 202, 208, 209, 300, 302, 316, DIG. 19; 383/44, 45, 48, 49; 422/26, 28, 40, 292, 293, 296, 297, 294

[56] References Cited

U.S. PATENT DOCUMENTS

| 2,092,445 | 9/1937 | Doulgheridis . |
| 2,633,284 | 3/1953 | Moffett et al. . |
| 2,634,856 | 4/1953 | Perkins . |
| 2,676,702 | 4/1954 | Whitefoot, Jr. . |
| 2,947,415 | 8/1960 | Garth . |
| 2,997,397 | 8/1961 | Doulgheridis . |
| 3,123,210 | 3/1964 | Hermanson et al. . |
| 3,229,813 | 1/1966 | Crowe, Jr. et al. . |
| 3,247,957 | 4/1966 | Kemble . |
| 3,468,471 | 9/1969 | Linder . |
| 3,498,742 | 3/1970 | Long ..................... 206/438 |
| 3,949,934 | 4/1976 | Goglio ................... 220/208 |
| 4,105,407 | 8/1978 | Sanderson . |
| 4,228,914 | 10/1980 | Sanderson . |
| 4,247,517 | 1/1981 | Sanderson . |
| 4,251,482 | 2/1981 | Sanderson . |
| 4,349,118 | 9/1982 | Sanderson . |
| 4,372,921 | 2/1983 | Sanderson . |
| 4,374,570 | 2/1983 | Sanderson . |

OTHER PUBLICATIONS

Brochure entitled "Open for Injection" published by the Sterelis Corporation.

Primary Examiner—Joseph Man-Fu Moy
Assistant Examiner—Jimmy G. Foster
Attorney, Agent, or Firm—Knobbe, Martens, Olson & Bear

[57] ABSTRACT

A bag for containing articles to be sterilized is automatically sealed by means responsive to a sterilizing environment applied to the bag. One or more actuators are releasably attached to the bag to automatically close one or more valves at the appropriate point in a sterilizing cycle to result in a vacuumized sterile package.

20 Claims, 16 Drawing Figures

U.S. Patent   Apr. 22, 1986   Sheet 1 of 3   4,583,643
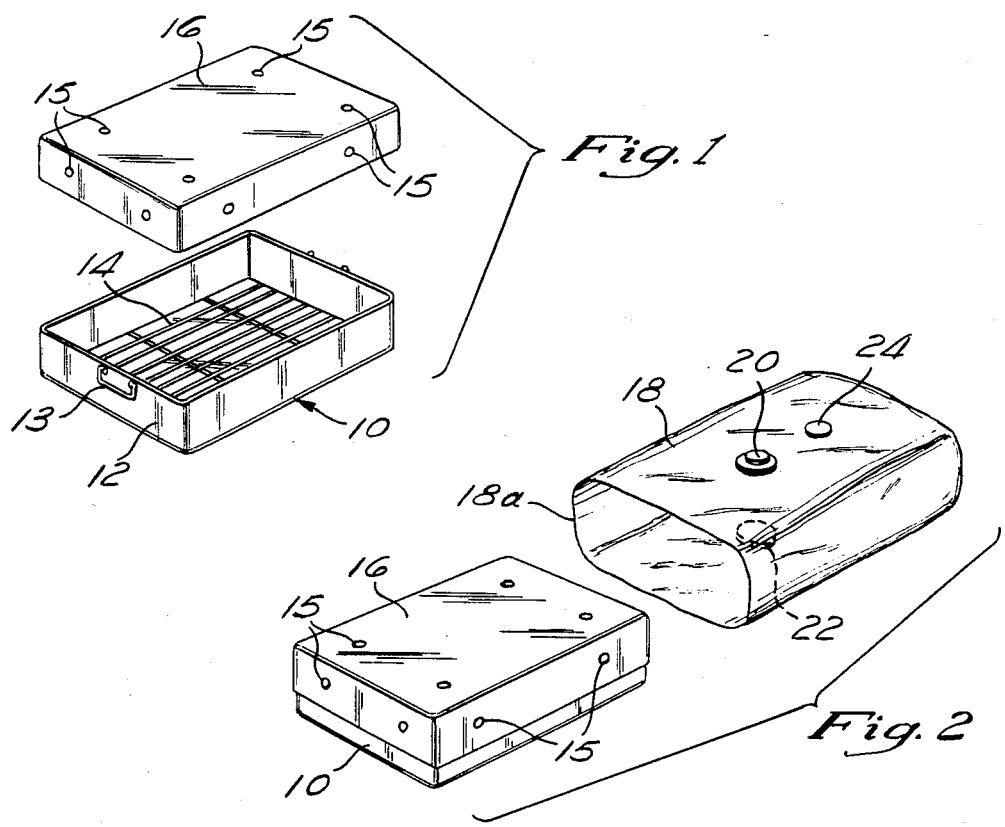
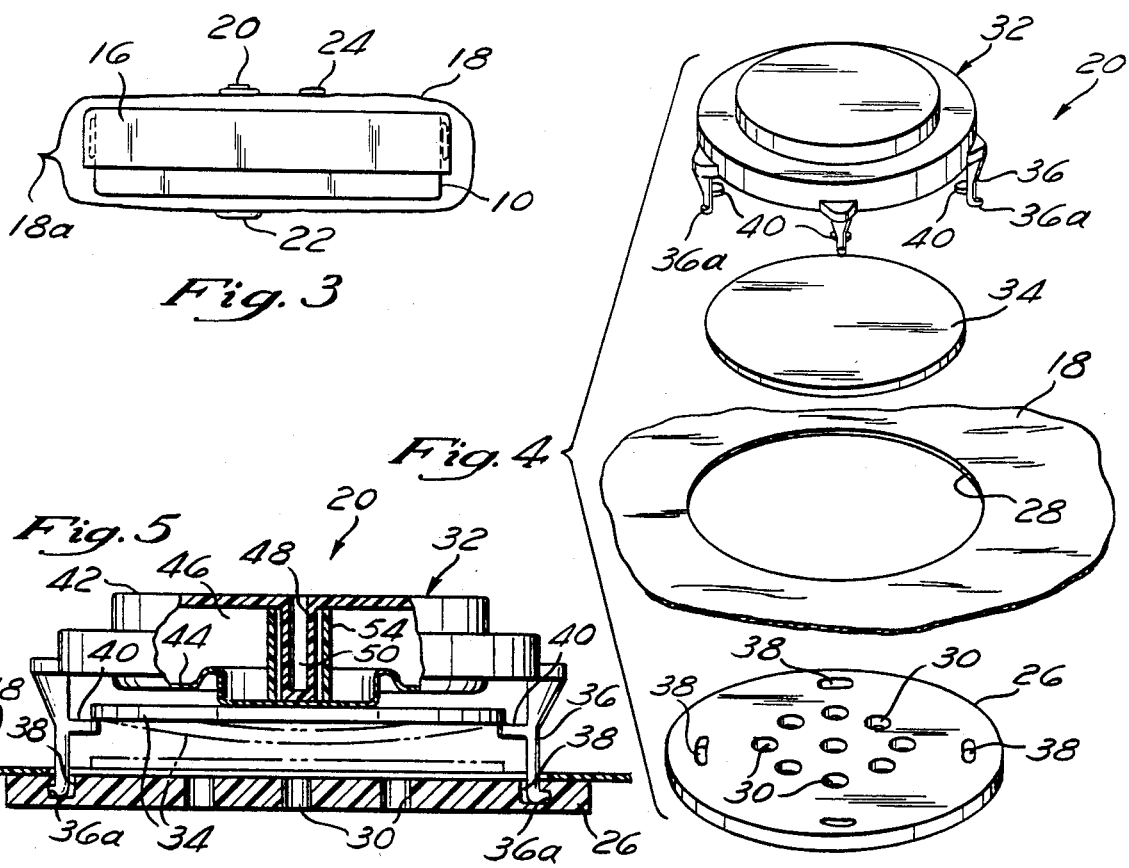

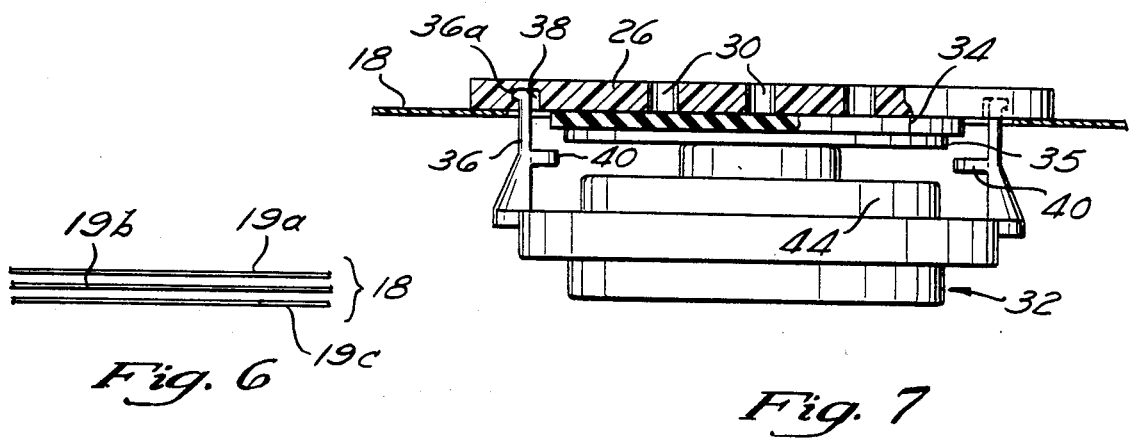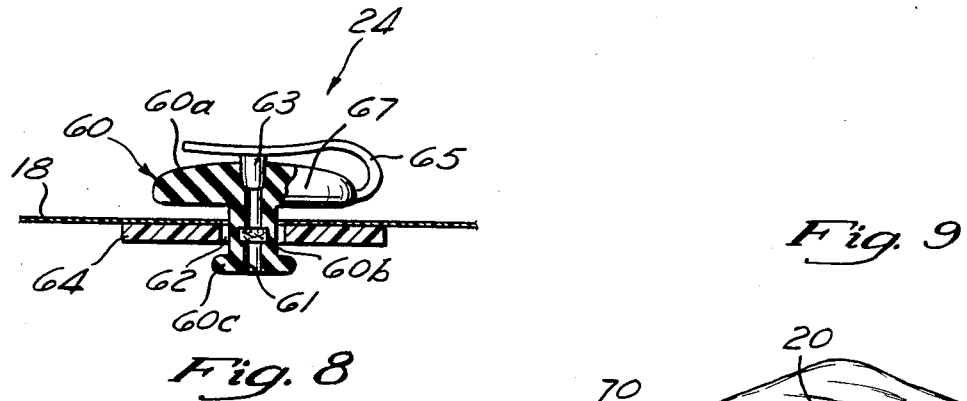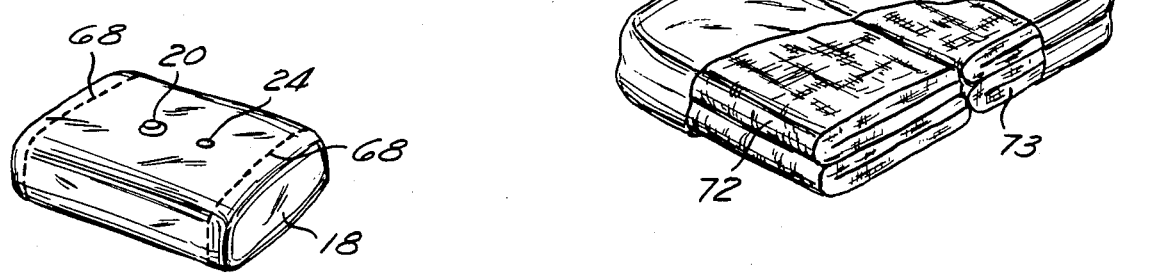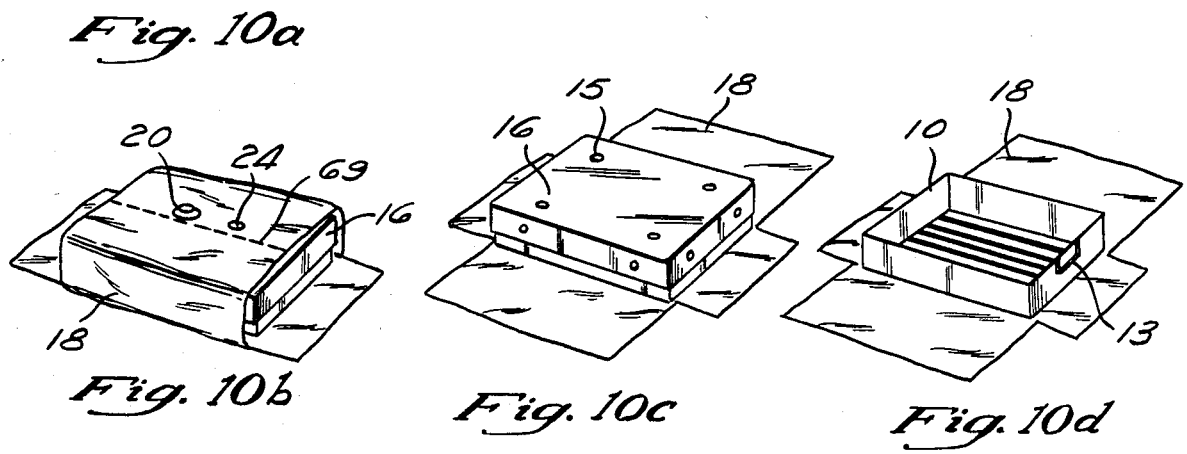

STERILE BAG

BACKGROUND OF THE INVENTION

This invention relates to apparatus for containing articles to be sterilized and stored, particularly medical items such as surgical instruments and linens. Reusable medical items that require sterilization before use, are typically wrapped in towels and placed in trays to be positioned in an autoclave. The towels provide some protection for maintaining sterility after the completion of the sterilizing operation, but of course this is limited since unsterile air penetrates the toweling as soon as the bundle is exposed to air from outside the autoclave, particularly if a vacuum sterilizing cycle is used.

In recent years, effort has been expended to improve this process by providing containers that are sealed at the completion of the sterilizing process so that sterility will be maintained until the container is open. Examples of such arrangements are shown in U.S. Pat. Nos. 4,247,517, 4,251,482 and 4,372,921. Since the containers in those patents are designed to provide a near atmosphere-free condition, so as to best maintain sterility, and since it is also desirable to see through the container to observe its contents, the containers have been made of strong, rigid plastic materials to withstand the near atmospheric pressure differential between the interior and the exterior of the container. The rigid container is also desirable from a standpoint of durability so that the containers can be reused for many years.

While the apparatus described in these patents works very well and is useful in hospitals and doctors' offices, in some situations a rigid exterior container is not needed and a need exists for a container that can practically be used once and then discarded. In addition to such a container being used for items that are to be sterilized and used, there is also now a need in hospitals for a container for toxic wastes that are to be sterilized and then transported to an incinerator.

SUMMARY OF THE INVENTION

In accordance with the present invention, there is provided a flexible bag for articles to be sterilized, wherein the bag is automatically sealed during a sterilizing cycle to maintain the sterility of the articles. When the bag is utilized to contain rigid, sharp articles such as surgical instruments, an inner, unsealed container encloses the articles so that the bag can collapse against the inner container without being punctured by sharp articles. Alternatively, if the bag is employed with soft materials where there are no sharp edges, an inner container is not required since the bag can simply collapse against the soft materials when the bag is vacuumized.

After the articles to be sterilized are placed into the bag, the bag is closed by heat sealing or other hermetic sealing means. One or more valves are provided in the walls of the bag to permit unsterile air to be withdrawn from the bag during the autoclave cycle and to be replaced by steam or other sterilizing fluids. Such valves remain open until near the end of the sterilizing cycle when they are automatically closed by actuator means, which are preferably responsive to changes in temperature and pressure occuring during the sterilizing cycle.

In a preferred form of the invention, there is provided a reinforcing or support plate secured to a wall of the bag to serve as the reaction surface for the automatic valve closing actuator. For example, a hole is formed in the bag and a small, stiff plate of plastic is heat-sealed or otherwise secured to the portion of the bag forming the periphery of the hole. The actuator is supported by the plate to hold a valve element in a valve open position and then move the element or allow it to move to a valve closing position at a desired point during the sterilizing cycle.

Preferably, the valve element is a flat, pliable pad so that when it has been moved to its valve closing position, the element will snugly engage the surface of the support plate, covering the valve opening or openings. With the valve closed, the pressure within the bag might temporarily exceed the pressure surrounding the bag, such that the flexible valve element will be slightly opened by the pressure differential, thereby acting as a relief valve. For example, vaporization of residual condensation in the bag could cause a pressure rise. With the relief valve feature, maximum vacuumization of the bag is obtained. Such a valve element is also advantageous for relieving the vacuum within the container when it is to be open. This factor is less significant when the container is in the form of a bag in that a wall of the bag can easily be severed to open it. However, the actuator mechanism is also useful with a rigid container, and in that situation the valve element can be simply peeled away from the surface of the container around the valve openings so as to relieve the vacuum within the container, and thus permit it to be opened.

Preferably, the bag is provided with a valve in its upper wall and a valve in its lower wall. This arrangement permits better circulation of the sterilizing fluid and displacement of the unsterile air within the bag at the beginning of the sterilizing cycle. In that situation the valve in the lower wall of the bag includes a thin but stiff plate that serves as a backing plate for the flexible valve element so that when the valve is to be closed, the actuator engages the backing plate and moves it and the valve sealing element into closing position on the opening in the bag. The valve actuator holds the backing plate and the valve element in the valve closed position until the end of the sterilizing cycle, at which time a vacuum occurs in the bag to hold the valve element in position even after the actuator is withdrawn or removed. Prior to the time that a vacuum exists within the container, the backing plate serves to distribute the actuator closing force sufficiently to make sure that the valve element is sealed on the valve opening. The valve in the upper wall of the bag, however, does not need the backing plate in that it is desirable that the periphery of the valve element be able to open slightly to relieve any pressure that might exist within the bag. Once the pressure is relieved, any portions of the pliable valve element not held in position by the actuator will simply fall by gravity into sealing position, and will ultimately be held there by the vacuum created within the bag.

Instead of the valves in the bag needing to be capable to also serve a pressure relief function, a separate pressure relief valve may be employed in the upper wall of the bag. The primary function of the pressure relief valve is in a so-called "gravity" autoclave wherein a vacuum cycle is not provided at the end of the sterilizing cycle. The pressure relief valve will permit heated vapor to escape from the bag if the pressure within the bag exceeds that outside the bag. Such condition may exist, for example, if the bag is allowed to remain in the autoclave in heated condition at the end of the sterilizing cycle so that any moisture within the bag may vaporize and escape from the bag. At the same time, the valve will prevent flow into the bag and thus maintain sterilization.

SUMMARY OF THE DRAWINGS

FIG. 1 is an exploded, perspective view of a container having a lower tray portion similar to the type currently used in autoclaves.

FIG. 2 is an exploded, perspective view illustrating the manner in which the container of FIG. 1 is to be positioned within a bag for sterilization purposes.

FIG. 3 is a side elevational view showing the inner container sealed within the bag.

FIG. 4 is an exploded perspective view illustrating the upper valve and actuator assembly for the bag.

FIG. 5 is a cross-sectional view of the valve and actuator assembly of FIG. 4.

FIG. 6 is an enlarged, fragmentary, cross-sectional view of the bag wall illustrating the layers of which it is made.

FIG. 7 is a partially sectionalized view of the lower valve and actuating assembly with the actuator extended, holding the valve closed.

FIG. 8 is a cross-sectional view of the separate relief valve which may be employed in the upper wall of the bag.

FIG. 9 is a perspective, partially sectionalized view of the bag containing a stack of linens.

FIGS. 10a, 10b, 10c and 10d illustrate the manner of opening a sterile package of the type shown in FIGS. 2 and 3.

Figure 11:
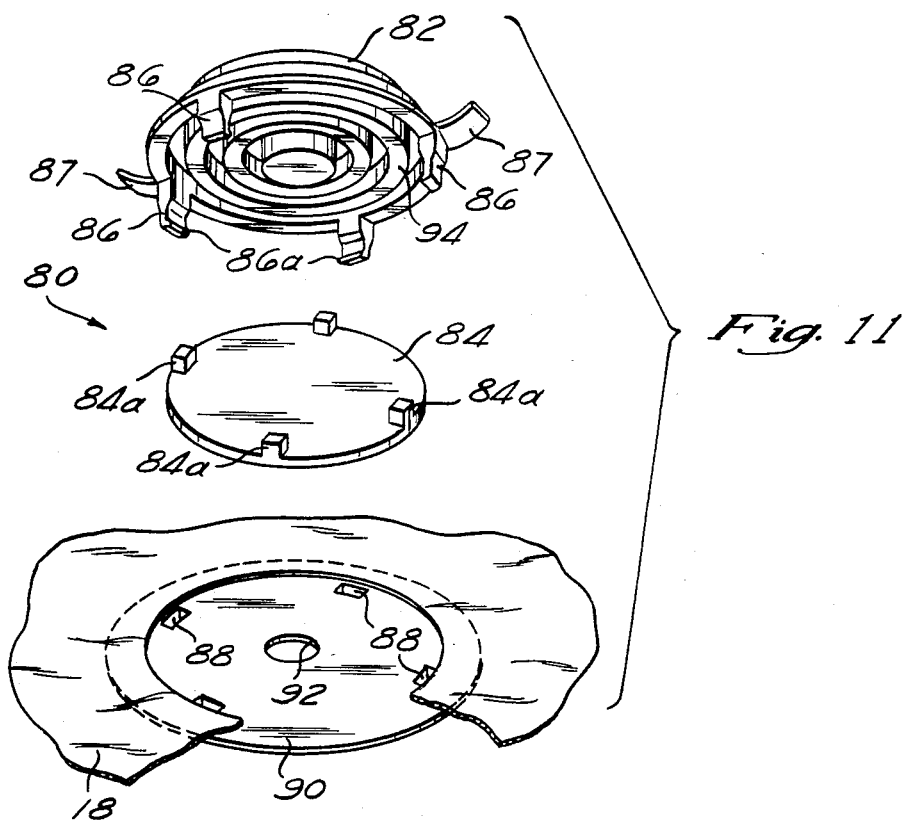
FIG. 11 is an exploded perspective view of an alternate valve and actuator assembly for the bag.

The container in FIG. 1 includes a tray 10 having a side wall 12 with handles 13 and a bottom grid 14 spaced upwardly somewhat from the lower edge of the side wall. This tray is similar to that currently used by hospitals for sterilizing medical items. For example, surgical instruments may be wrapped in a towel and placed in the open tray 10, or the tray may be wrapped entirely in a double layer of linen which is then lifted and placed in an autoclave. However, for the present invention, a cover 16 is positioned on the tray with its side walls extending around the upper edges of the tray and downwardly far enough to cover the tray handles. With the grid bottom, and with a plurality of holes 15 in the cover, the container is, of course, not sealed.

In accordance with the invention, surgical instruments or other items to be sterilized may be placed directly in the tray 10, the lid placed on the tray, and the covered but unsealed container inserted into the open end 18a of a flexible, air and steam impermeable bag 18, as seen in FIG. 2. The open end of the bag is then hermetically sealed as seen in FIG. 3. The bag and its contents are then inserted into a sterilizing apparatus such as a steam autoclave, typically found in hospitals and medical offices.

In addition to being impervious to air and steam, the bag should be sufficiently tough to not readily puncture when the tray is placed into it and the assembly is placed into the autoclave. Also, it is preferably made in a manner such that it can be closed by the heat sealing process. Further, it should be sufficiently inexpensive that it is practical to dispose of it after a single use. FIG. 6 illustrates a preferred form of the bag having a laminated construction with an inner layer 19a formed of polypropylene which is heat-sealable and of moderate strength and air impermeability. Adjacent this is positioned a layer 19b of polyester, sold under the trademark Mylar, which adds strength to the bag. Adjacent the Mylar layer is an outer membrane 19c of thin, tough, air-impervious material such as polyvinylidene, commonly sold under the trademark Saran. This laminated bag construction provides the desired characteristics.

In the top wall of the bag is positioned a valve and actuator assembly 20. A similar assembly 22 is positioned in the lower wall of the bag. Also shown in FIGS. 2 and 3 is a pressure-relief valve 24, which might also be called a "drying" valve.

Referring to FIGS. 4 and 5, it may be seen that the valve and actuator assembly 20 includes a stiff support plate 26, preferably made of a plastic material that can be heat-sealed to the bag 18 when positioned in contact with the inner polypropylene layer 19a of the bag. More specifically, a hole 28 is cut in the bag slightly smaller than the plate, and the bag material surrounding the hole is heat-sealed to the upper surface of the plate adjacent its periphery. The plate is formed with one or more holes 30 which serve as valve openings for permitting fluid flow into and out of the bag.

Supported on the exterior of the bag on the upper surface of the plate 26 is an actuator 32 carrying a valve element 34, utilized to close the valve openings 30. The actuator has a plurality of legs 36 which cooperate with a corresponding group of shallow slots 38 formed in the outer or upper surface of the plate as viewed in FIG. 5. These slots are partially undercut so that when the feet 36a forming the lower ends of the actuator legs 36 are inserted in the slots, the feet on the legs may be captured and held in position by the support plate. The slots are positioned around the valve openings 30, but they do not extend through the plate.

On the inner portion of each of the actuator legs 36, spaced inwardly from the foot 36a, there is formed an inwardly-extending support 40 which cooperates with the periphery of the valve element to hold the valve element in its raised position as shown in FIG. 4. The valve element is preferably formed of a resilient, pliable material that will readily conform to the support plate 26 as shown in phantom lines in FIG. 5.

The actuator 32 includes an upper shell 42, preferably made of a moldable, stiff plastic and preferably formed integral with the actuator legs 36. Secured to the lower portion of the shell 42 is a bellows wall 44, which in combination with the shell 42 defines an expandable chamber 46. The bellows wall is preferably made of a thin plastic material that can be suitably secured at its periphery to the surrounding shell 42. Further, as may be seen from FIG. 5, the bellows wall has concentric corrugations that permit the sections to move in the manner of a bellows.

Formed integral with the upper wall of the shell 42 is a centrally-located tubular projection 48 that is open at its upper end and closed at its lower end. A plurality of valve openings 50 are formed in the side wall of the projection 48. Loosely surrounding the projection 48 is a valve element in the form of a tubular sleeve 54 made of heat-shrinkable material.

The valve and actuator assembly 22, shown in FIG. 7, is identical to the assembly 20 of FIG. 5, with the exception that there is provided a stiff backup plate 35 which extends between the valve element 34 and the nose of the bellows wall 44. The backup plate is preferably slightly smaller in diameter than the valve element 34 so that it does not interfere with the supports 40 on the actuator legs 36.

The relief valve 24 of FIGS. 2 and 8 includes a one-piece valve element 60 made of a resilient, pliable elastomeric material. The element has an enlarged upper portion 60a having a flat, lower surface, a neck portion 60b, and a lower retainer portion 60c. A valve opening 62 is formed in the bag 18 and a support plate 64 attached to the bag. Thus, the bag, backed by the plate 64, forms a valve seat with respect to the valve opening 62. The valve stem 60b, which extends through the valve opening 62, is considerably smaller in diameter than the opening, creating a rather loose fit. Thus, if the valve element is in a closed position wherein the lower surface of the upper portion 60a is sealed against the bag, and the pressure on the inside of the bag, which is the lower side as viewed in FIG. 8, increases to the point where it exceeds the pressure on the outside of the bag, the valve element 60 will move upwardly into an open position as shown in FIG. 8, allowing pressure within the bag to be vented by way of the opening 62. As soon as the pressure within the bag drops to that of the pressure outside of the bag, the valve element 60 will fall into closed position.

The valve element 60 may also be provided a passage 61 extending axially through the portions 60a, 60b, and 60c. This passage is closed by relief plug 63 positioned on the end of a strap 65 attached to the periphery of the upper portion 60a. A biological filter 67 is positioned within the passage 61.

OPERATION

(a) Vacuum Autoclave

As briefly explained above, articles to be sterilized are placed within the tray 10, shown in FIG. 1. The lid 16 is then positioned on top of the tray, the closed container inserted into the plastic bag as shown in FIG. 2, and the bag sealed as shown in FIG. 3. The package is placed into an autoclave, such as a conventional steam autoclave commonly found in hospitals and doctor's offices. There are a variety of autoclaves in use. Consider first the so-called vacuum autoclave having one or more initial vacuum phases for withdrawing unsterile air, followed by a steam phase and a final vacuum.

A valve and actuator mechanism 20 of the type shown in FIG. 5, is positioned in the upper wall of the bag, as shown in FIG. 2. The valve element 34 is carried by the actuator at that time so that the holes 30 through the support plate 26 are open. A valve and actuator assembly 22, of the type shown in FIG. 7, is positioned in the bottom wall of the bag as shown in FIG. 2. This valve includes the backup plate as discussed above, and the valve element is carried by the actuator as in FIG. 5 such that the valve openings leading into the valve are open. That is, the valve element as viewed in FIG. 7, would be in a lower position spaced from the bag, similar to that shown for the seal 34 in FIG. 5.

If the bag includes a valve 24 positioned in the top wall as shown in FIG. 2, the valve element 60 would initially be in its lower position with its upper portion 68 engaging the bag. It would be in this position simply by virtue of gravity.

When a vacuum is applied by the autoclave, the vacuum is similarly applied to the interior of the bag since the two valves 20 and 22 are open. Also, the vacuum is applied to the chamber 46 in the actuator 32 by virtue of the openings 50 in the projection 48 in the actuator shell 42. When high-pressure steam is applied by the autoclave, the steam flows into the bag through the openings 30 of the valves 20 and 22, and any residual air within the bag is displaced through the holes 30 in the lower wall of the bag. The steam is continued to be applied to the autoclave for whatever period of time is necessary to sterilize the container and its contents. The steam is then withdrawn, utilizing the assistance of a final vacuum phase, which completes the sterilizing cycle.

The temperature of the steam causes the heat-shrinkable sleeve 54 in the actuator to shrink inwardly; thus closing the valve openings 50 and capturing a quantity of steam within the chamber 46.

When the steam phase is ended and the pressure within the autoclave drops, the steam captured within the chamber 46 will cause the chamber to expand by virtue of the pressure drop outside of the chamber. This causes the lower bellows wall 44 of the actuator to move downwardly as shown in FIG. 5, pushing the valve element 34 and releasing it from the supports 40 on the actuator leg, and pushing it into sealing engagement with the plate 26 over the openings 30 leading into the bag. Gravity, of course, assists this movement with the assembly in the upper wall of the bag. Note that the actuator shell and legs are held stationary by reacting against the support plate.

Simultaneously, the actuator 22 in the lower wall of the bag is expanding to the position shown in FIG. 7 wherein the valve element 34 has been raised by the actuator, together with the backup plate 35, into the closed position. Note that the backup plate is required for this operation in that the nose of the bellows wall 44 for the actuator of FIG. 7 would engage only the central portion of the element 34. Thus, it is possible that the pliable valve element might not be completely closing the outer valve openings 30 without the backup plate. Of course, a different valve opening or bellows construction could be employed that would make the plate 35 unnecessary. Varying the thickness of the valve element to make it inflexible would likewise replace the need for a support plate.

During the final vacuum phase, the edges of the valve element 34 of the upper valve assembly 20 will lift upwardly if the pressure on the exterior of the bag is lower than that of the interior of the bag. Thus, any residual moisture in the bag will be vaporized by the vacuum and allowed to excape from the bag. However, once the bag has been evacuated and the interior and exterior pressures equalized, the periphery of the valve element 34 will return by gravity to the fully-closed position. Thus, the valve element 34 will function as a one-way check valve to permit flow out of the bag but to prevent flow into the bag. This insures that the bag is vacuumized.

When atmospheric pressure is allowed into the autoclave, the increased pressure on the exterior of the bag will urge the valve elements 34 of both assemblies 20 and 22 more tightly into the closed position, in view of the vacuum within the bag. Also, the actuators will continue to urge the valve elements into the closed position until the expandable chamber 46 has cooled sufficiently to cause the bellows wall 44 to retract. The bag material is, of course, sufficiently strong to maintain a vacuum within the bag which is supported by the inner container or bag contents, such as sheets.

When the sterilized bag is removed from the autoclave, the actuators 32 may be removed from the bag by pressing the actuator legs 36 inwardly slightly to release them from the retaining slots 38. The valve elements 34 will, of course, remain in position, being held there by the vacuum that exists within the bag. With the actuators removed, the sterilized bags and their contents may be more easily stacked in storage.

(b) Use of Bag Contents

When the contents of the bag are to be utilized, the bag may be carried directly to the general use area. The bag is then opened in a predetermined sequence to maintain the sterility of the interior tray and its contents. As a first step, the ends of the bag are cut or opened along the top and sides along the broken lines 68 indicated in FIG. 10a. The cutting may be performed by utilizing a scissors, or by use of a suitable tear string, which is also represented by the lines 68. Next, a cut is made by scissors or tear string along the broken line 69 illustrated in FIG. 10b down the mid-section of the upper wall of the bag. The cut edges of the bag are unwrapped and laid flat as shown in FIG. 10c. Note that any dust or contamination from the exterior of the bag that may have fallen onto the container when the bag is opened should strike the cover 16 rather than the contents of the tray. The cover holes 15 are not beneath the cut 69. Thus, the interior of the container is protected by both the bag and the cover. The cover is then removed. The open, sterilized tray with its sterilized contents is carried by a person wearing sterilized gloves, utilizing the handles 13, to the immediate operating area. Thus, the contents of the tray are available for use directly from the tray in sterile condition.

If desired, the vacuum in the bag may be first released by peeling back one of the valve elements which are being held in position by the vacuum. Incidentally, if a particular valve element is not held tightly against the bag, this indicates that a vacuum no longer exists within the bag and the contents of the bag have been contaminated to some extent. Of course, the package is still at least as good as it would have been with the old "wrapped in a towel" approach, as has been used for many years.

(c) Relief Valve

With the operation as described in the preceeding paragraphs, the relief valve 24 in the upper wall of the bag is not necessarily needed, since the valve element 34 of the upper assembly 20 functions as a relief valve, as has been described. However, the relief valve 24 might be provided simply as a redundancy for insuring more complete vacuumization of the bag. Alternatively, the upper assembly 20 could be provided with a backup plate for its valve element 34 as with the lower assembly 22. This provides more positive initial positioning and closing of the valve element, and the element would then not function as a relief valve since the backup plate would hold the valve element in closed position so long as the expandable chamber 46 is applying a closing force onto the backup plate. In that case, the valve 24 would be providing the only pressure relief function during the final vacuum phase of the sterilizing cycle. The pressure relief valve 24 also functions as a pressure release when the bag is to be opened in that the upper element 60a may be peeled away from the surface of the bag to allow communication through the hole 62. Alternatively, the plug 63 may be removed from the passage 61 by pulling upwardly on the end of the strap 65 against the plug. The air flowing into the chamber by way of the passage 61, will be filtered by the filter 6.

(d) Gravity Autoclave

With a so-called "gravity" autoclave, there is no final vacuum phase and there may be no preliminary vacuum phases. In that case, the pressurized steam is simply directly introduced to the autoclave. The valve and actuator assemblies 20 and 22 would function as during the steaming phase of the vacuum autoclave. Having two valve and actuator assemblies is particularly important in that situation to insure that the air initially within the bag can be displaced through the valve 22 when the steam is entering through the valve 20. When the steam phase of the cycle is completed and the pressure returns to atmospheric, the expandable chamber 46 in each of the actuators will, once more, expand to close the valve as described above. If the autoclave is then opened to atmosphere, while the heating operation continues in the autoclave, any residual vapor created by the heat that causes a pressure greater than atmosphere within the bag, will cause the valve in the upper wall of the bag to open, thus in effect, drying the contents of the bag. With this arrangement, the interior of the bag is not made quite as atmosphere-free as with the vacuum autoclave, but a vacuum is nevertheless created when the heating operation is stopped and the bag and its contents are allowed to cool. Note that the actuators will continue to hold the valve elements closed until the temperature within the expandable chambers drops, causing the pressure to drop. As the pressure within the chamber 46 drops, the pressure in the bag will likewise be dropping due to the decreased temperature with the result that the vacuum being formed will hold the valve elements 34 in closed position.

Thus, with either type of autoclave cycle described above, the pressure within the bag at the completion of the operation is less than that outside the bag. This pressure differential causes the bag to be withdrawn against the rigid surfaces of the interior container 10 including the cover 16. The cover is advantageous when some of the items within the container 10 hae sharp points, such as surgical instruments.

For a further understanding of "vacuum" and "gravity" autoclave cycles, reference may be had to the abovementioned patents that show pressure temperature graphs of the cycles, as well as the automatic closing of containers of expandable chamber actuators.

(e) Use of Bag or Linens

As mentioned above, the bag is useful for sterilizing linens, as shown in FIG. 9, without the use of a rigid interior container. In that situation, the walls of a bag 70 are merely drawn directly against the linens 72 and a protective layer of cloth or plastic 73 and no other supporting surface is required. This condition of the bag being drawn against the linens makes it easy for an observer to tell that the package is in sterilized condition. Removing the valve elements 34 usually confirms this fact in that the sound of air rushing into the bag is heard, when the vacuum is released. The bag in FIG. 9 is opened as described in connection with FIG. 10, the protective layer 73 being last to be removed.

(f) Use of Bag for Toxic Wastes

As mentioned above, the bag is also useful for containing toxic wastes in a hospital. There are many types of such materials, one example being bandages or dressings on a wound or other conditions that are highly contagious. In the past, such materials have usually simply been placed in bags and shipped to an incinerator without any interim treatment or special handling. This means that personnel along the handling and transportation chain or path may be exposed to such materials. Currently a need is arising to subject such materials to a sterilizing cycle, and they should be sealed to prevent exposure to others.

Thus, when the bag is used for toxic materials, the materials would be placed into the bag in the area where they are generated, the bag sealed, the actuator and valve assemblies attached, and the bag placed in an autoclave or other sterilizing apparatus. The valves would close at the desired point in the cycle as described above, such that the bag can be safely handled. Since there is great concern of all bacteria in the bag not being destroyed, the sealed waste is safely transported to a disposal site for incineration.

Figure 13:
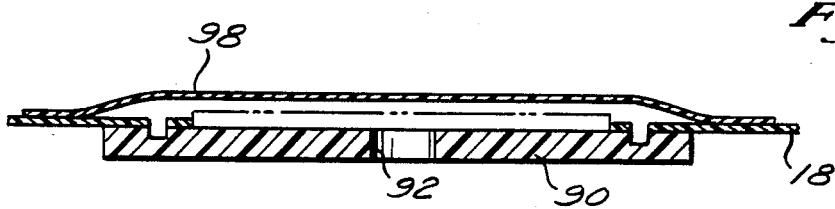
FIG. 13 is a schematic showing of a seal over the bag valve opening.

In many cases, the waste material is generated in a location somewhat remote from sterilizing apparatus. Thus, to prevent the escape of noxious gas in transportation of the bag, the bag may be provided with removable gummed seals 98 over the valve openings, as shown schematically in FIG. 13. After the bag is transported to the sterilizing apparatus, the seals are removed and replaced by the actuator assemblies. A similar seal may be placed over the valve element after a sterilizing operation to prevent inadvertent removal of the valve element. This is useful for any uses of the bag.

A separate drawing for the toxic waste use of the bag is not shown, since visually it is like the bag of FIG. 9 except that there would be no need for the protective shield 73, and the shape of the bundle would usually be irregular rather than having neatly stacked contents.

(g) Other Uses of Valves and Actuators

It should be recognized that the valve and actuator assemblies 20 and 22 may be employed in connection with rigid containers as well as flexible bags, with suitable grooves or sockets formed in the rigid container for receiving the legs of the actuator. Alternatively, other suitable arrangements for securing the actuator legs to the container may be provided. Similarly, the valve 24 may be useful with rigid containers.

(h) Gas Sterilizing Cycle

While the operation of the device is described above as being used in connection with a steam sterilizing cycle, it should be recognized that the bag and the actuator and valve assembly is also useful in connection with a gas sterilizing system. Typically, the sterilizing gas is applied at some elevated temperature and pressure and it is later desirable to apply a vacuum to withdraw the sterilizing gas. The actuator described above will accommodate such action, closing the valve and the bag automatically and yet allowing the gas to be quickly evacuated, leaving the container and its contents in a sterilized, vacuumized condition. This approach may not only be useful in hospitals but also in commercial applications wherein it is desirable to furnish new products in a sterilized, vacuumized condition. Currently, gas is frequently applied to objects to be sterilized in a sealed bag having a paper wall or walls of a plastic material that permit the gas to penetrate the bag. One of the difficulties with this approach is that a high vacuum applied to the bag at the end of the sterilizing cycle will likely rupture the bag since the porosity of the bag is such that a significant pressure differential can temporarily exist between the interior and exterior of the bag. To avoid this, the finished products are often allowed to sit for a considerable period of time while the gas within the bag is allowed to circulate by normal molecular movement to be largely replaced by air which is filtered through the bag walls. In addition to this delay, the porous bag approach has the further significant disadvantage that some bacteria can pass through the bag walls whereas applicant's bag will not permit air to enter and the product is confined in a sterile, vacuumized state.

ALTERNATE CONSTRUCTION OF FIGS. 11 AND 12

Figure 12:
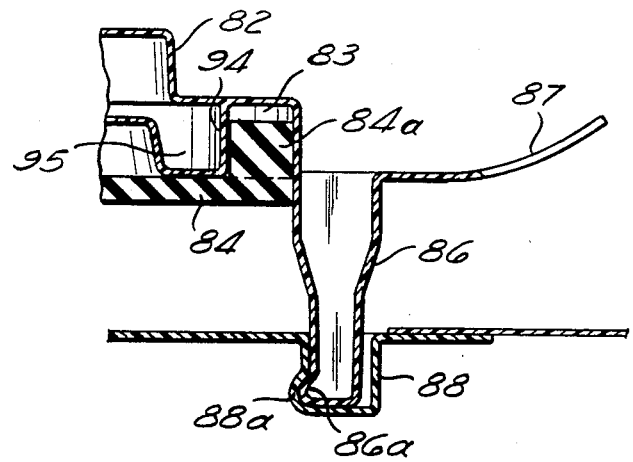
FIG. 12 is an enlarged, cross-sectional view of a portion of the assembly of FIG. 11.

The actuator and valve assembly 80 of FIGS. 11 and 12, functions essentially like the assembly of FIGS. 4 and 5 but it has certain manufacturing advantages. The primary advantage is that the upper shell 82 which supports the valve element 84, has a plurality of legs 86 which are formed in combination with the shell and can be made by a vacuum-forming process, which is less costly for small volume than is an injection-molding process. As may be seen from FIG. 12, the leg 86 has a hollow configuration being open at its upper end and closed at its lower end. This lower end is also provided with an inwardly extending protuberance or foot 86a. Formed integral with the upper, radially outer side of the leg is an outwardly extending finger tab 87 for the convenience of grasping the actuator and for releasing the actuator from its retaining plate. Note that the configuration of the shell 82 is such that it can readily be made by the vacuum-forming process including the slightly inwardly extending locking foot 86a.

The pliable seal 84 is formed with a plurality of retaining lugs 84a, that extend upwardly from the top surface of the valve element 84. These lugs are sized to fit within the annular recess 83 around the periphery of the bellows wall 94. Thus, the valve element 84 is held in its valve-open position by this simple wedging action.

A support plate 90, on which the actuator is mounted, is heat-sealed to the portions of the bag 18 surrounding an enlarged opening in the bag. Within the support plate there is formed a plurality of sockets 88 which are closed at the lower end, open at the upper end, and shaped to receive the legs 86 of the upper shell. These sockets are formed with slightly inwardly-extending recesses 88a for receiving the feet on the ends of the legs, as may be seen in FIG. 12.

Although not shown in FIG. 11, the actuator includes a valve arrangement like that shown in FIG. 5 for capturing a quantity of heated sterilizing fluid. In operation, the chamber 95 formed by the upper shell and the bellows walls, expands at the appropriate time and causes the nose of the inflatable chamber to urge the valve element 84 into its closed position, covering an opening 92 in the support plate. At the completion of the sterilizing cycle when the actuator is to be removed from the bag, it is only necessary to grasp the two outwardly extending finger tabs 87 and inch them towards each other. That is, the outer ends of the tabs are urged upwardly and inwardly, applying a force on the adjacent leg 86 which urges the feet on those legs outwardly to release them from the recess formed in the socket of the support plate. The actuator can then be withdrawn, even though the feet on the two legs not having finger tabs still provide some retaining force.

What is claimed is:

1. Apparatus for containing articles to be sterilized in a steam autoclave or the like, comprising:
a flexible, impermeable bag; and
a valve and actuator assembly mounted in a wall of the bag for permitting sterilizing fluid into the bag during a sterilizing cycle and for closing the bag when the articles therein have been sterilized, but before the bag is exposed to unsterilized environment, said assembly including a stiff support member sealingly secured to the bag and having a valve opening therein, and an actuator for automatically closing the valve opening on said support member, said actuator and said support member having interconnecting means for releasably supporting said actuator on said support member, a valve element, said actuator having means for releasably holding the valve element in a valve open position adjacent said opening, said actuator further including means for providing a force to move said valve element into a valve closed position covering said opening with said actuator reacting against the member during the closing operation.

2. The apparatus of claim 1, wherein said force providing means is responsive to changes in the temperature and pressure of the sterilizing fluid.

3. The apparatus of claim 1, wherein said support member is a stiff plastic plate secured at its periphery to the flexible bag, with said valve opening being positioned inwardly from the connection between the plate and bag.

4. The apparatus of claim 3 wherein said force providing means includes an expandable chamber having means for capturing a quantity of steam applied to the bag during a sterilizing cycle to utilize the captured steam as an actuating force to close the valve element when the pressure around the chamber is reduced.

5. The apparatus of claim 4 wherein said actuator connecting means includes a plurality of legs which are releasably secured to said plate in a position to hold the valve element spaced from but aligned with the valve opening so that when the expandable chamber expands, the valve element is moved into valve closing position.

6. The apparatus of claim 1 wherein said assembly includes a backing plate carried by said actuator and engaging said valve element to support the valve element while the expandable chamber is urging the backing plate together with the valve element into valve closing position.

7. The apparatus of claim 6 including a pair of said assemblies with one assembly without the backing plate positioned in an upper wall of the bag and an assembly with the backing plate positioned in a lower wall of the bag.

8. The apparatus of claim 1 including a rigid inner container positioned within said bag for containing articles to be sterilized and for supporting the bag when a vacuum is created within the bag.

9. The apparatus of claim 1 including a plurality of linens within the bag to be sterilized and to support the bag when a vacuum is formed in the bag during the sterilizing operation.

10. The apparatus of claim 1 including toxic waste material in the bag to be sterilized and to support the bag when a vacuum is formed in the bag during the sterilizing operation.

11. Apparatus for containing articles to be sterilized and stored, comprising:
a container in which the articles are to be positioned;
means forming a valve opening in the container;
an actuator including a plurality of legs;
means formed on said container and on said legs for releasably supporting the actuator on the container; and
a valve element releasably carried by said actuator and positioned so that it overlies but is spaced from the valve opening, said actuator including means for automatically moving said valve element into valve closing position at a desired point in a sterilizing cycle.

12. The apparatus of claim 11 wherein said valve element is made of pliable material, such that it is held in valve closing position by a vacuum existing within the container.

13. The apparatus of claim 11 wherein said actuator includes an inflatable chamber having valve means for capturing a quantity of steam within the chamber during a sterilizing cycle, said steam causing the actuator to expand when the pressure surrounding the chamber reduces, such that the valve element is moved to its closing position near the completion of a sterilizing cycle to ensure that the container is closed before it is exposed to unsterile environment.

14. The apparatus of claim 13 wherein the expandable chamber valve means includes a temperature responsive element which automatically closes the chamber to capture a quantity of sterilizing fluid.

15. The apparatus of claim 11 wherein said actuator means for automatically moving the valve element includes an expandable chamber having a movable wall with an annular groove formed adjacent the periphery of the movable wall and said valve element includes means which fits within said annular groove in a manner such that the valve element is supported by the actuator, but is releasable from the actuator when it is moved as the actuator expandable chamber expands.

16. A valve and actuator assembly for use with a container having a wall with a valve opening therein comprising: an actuator shell and a movable wall defining an expandable chamber, the movable wall being secured at its periphery to the shell, a plurality of legs formed on the shell and extending away from the shell on the side of the movable wall for mounting the legs into mating sockets supported in the wall of the container surrounding the container valve opening.

17. The assembly of claim 16 wherein said legs are hollow members located around the periphery of the shell in a manner such that the shell, together with the legs, may be formed as an integral unit by a vacuum-forming operation.

18. The assembly of claim 16 wherein the movable wall has a groove adjacent its periphery, and said valve element has means formed thereon which fits into said groove to support the valve element.

19. The assembly of claim 17 including tabs on said shell for grasping the actuator and for deflecting said legs to release the actuator from the mating sockets.

20. The assembly of claim 16 including foot means on said legs for releasably securing the actuator to said sockets.

* * * * *